United States Patent
Preiss-Bloom et al.

(10) Patent No.: US 12,295,616 B2
(45) Date of Patent: May 13, 2025

(54) CANNULATED IMPLANT DELIVERY DEVICE WITH ADJUSTABLE INSERTION DEPTH

(71) Applicant: OSSIO LTD., Caesarea (IL)

(72) Inventors: Orahn Preiss-Bloom, Caesarea (IL); Shay Parag, Caesarea (IL); Tal Zeevi, Caesarea (IL)

(73) Assignee: OSSIO LTD, Caesarea (IL)

( * ) Notice: Subject to any disclaimer, the term of this patent is extended or adjusted under 35 U.S.C. 154(b) by 364 days.

(21) Appl. No.: 17/859,039

(22) Filed: Jul. 7, 2022

(65) Prior Publication Data

US 2023/0024165 A1    Jan. 26, 2023

Related U.S. Application Data

(60) Provisional application No. 63/223,150, filed on Jul. 19, 2021.

(51) Int. Cl.
*A61B 17/34* (2006.01)
*A61B 17/00* (2006.01)

(52) U.S. Cl.
CPC .............. *A61B 17/3468* (2013.01); *A61B 2017/00681* (2013.01); *A61B 2017/00964* (2013.01)

(58) Field of Classification Search
CPC .. A61B 17/3468; A61B 17/88; A61B 17/8872
See application file for complete search history.

(56) References Cited

U.S. PATENT DOCUMENTS

| | | | |
|---|---|---|---|
| 4,033,043 A | * | 7/1977 | Cunningham ......... A61B 17/88 33/542 |
| 4,655,777 A | | 4/1987 | Dunn |

(Continued)

FOREIGN PATENT DOCUMENTS

| | | |
|---|---|---|
| CN | 1168105 A | 12/1997 |
| CN | 1214939 A | 4/1999 |

(Continued)

OTHER PUBLICATIONS

Extended European Search Report issued in App. No. EP23174959, dated Oct. 9, 2023, 10 pages.

(Continued)

*Primary Examiner* — Si Ming Ku
(74) *Attorney, Agent, or Firm* — GRAESER ASSOCIATES INTERNATIONAL INC; Dvorah Graeser

(57) ABSTRACT

A device, system and method for delivery of an implant having an adjustable length. The device is for inserting an implant at an appropriate tissue depth according to a depth finding placeholder, wherein the implant is suitable for insertion to a subject, the device comprising a cannula for receiving the depth finding placeholder and an adjustable depth of insertion element, wherein the adjustable depth of insertion element is adjusted to determine the appropriate tissue depth. The depth finding placeholder may include but is not limited to a wire, such as a K-wire for example. The cannula preferably comprises an opening of sufficient diameter to permit insertion of the depth finding placeholder. The cannula optionally comprises depth indicators, for example by being optionally marked with depth indicator markings. The device preferably comprises a transparent window, or optionally may comprise, additionally or alternatively, an open aperture and/or a viewing screen, to enable the depth indicators to be viewed.

20 Claims, 3 Drawing Sheets

(56) References Cited

U.S. PATENT DOCUMENTS

| | | |
|---|---|---|
| 4,750,905 A | 6/1988 | Koeneman |
| 4,911,718 A | 3/1990 | Lee |
| 5,064,439 A | 11/1991 | Chang |
| 5,181,930 A | 1/1993 | Dumbleton |
| 5,192,330 A | 3/1993 | Chang |
| 5,312,669 A | 5/1994 | Bedard |
| 5,338,772 A | 8/1994 | Bauer |
| 5,522,817 A | 6/1996 | Sander |
| 5,522,904 A | 6/1996 | Moran |
| 5,674,294 A | 10/1997 | Bainville |
| 5,679,299 A | 10/1997 | Gilbert |
| 6,004,650 A | 12/1999 | Schweizer |
| 6,171,338 B1 | 1/2001 | Talja |
| 6,299,649 B1 | 10/2001 | Chang |
| 6,306,140 B1 | 10/2001 | Siddiqui |
| 6,352,667 B1 | 3/2002 | English |
| 6,471,707 B1 | 10/2002 | Miller |
| 6,511,511 B1 | 1/2003 | Slivka |
| 6,602,293 B1 | 8/2003 | Biermann |
| 6,916,321 B2 | 7/2005 | Tenhuisen |
| 7,541,049 B1 | 6/2009 | Pertti |
| 7,918,879 B2 | 4/2011 | Yeung |
| 7,947,069 B2 | 5/2011 | Sanders |
| 8,702,716 B1 | 4/2014 | Stein |
| 8,709,055 B2 | 4/2014 | Beyar |
| 8,735,504 B2 | 5/2014 | Clay |
| 8,992,622 B2 | 3/2015 | Ullrich, Jr. |
| 9,186,302 B2 | 11/2015 | Kilway |
| 9,456,890 B2 | 10/2016 | Day |
| 10,926,004 B2 | 2/2021 | Preiss-Bloom |
| 2005/0118326 A1 | 6/2005 | Anfinsen |
| 2005/0177245 A1 | 8/2005 | Leatherbury |
| 2005/0216016 A1 | 9/2005 | Contiliano |
| 2005/0226904 A1 | 10/2005 | Choi |
| 2005/0228500 A1 | 10/2005 | Kim |
| 2006/0020266 A1 | 1/2006 | Cooper |
| 2006/0095134 A1 | 5/2006 | Trieu |
| 2006/0154206 A1 | 7/2006 | Petersson |
| 2006/0178748 A1 | 8/2006 | Dinger, III |
| 2007/0150059 A1 | 6/2007 | Ruberte |
| 2007/0185568 A1 | 8/2007 | Schwartz |
| 2007/0270969 A1 | 11/2007 | Schmid |
| 2007/0282455 A1 | 12/2007 | Luginbuehl |
| 2008/0255561 A1 | 10/2008 | Tormala |
| 2009/0112317 A1 | 4/2009 | Li |
| 2009/0234387 A1 | 9/2009 | Miller |
| 2009/0240337 A1 | 9/2009 | Myung |
| 2009/0258965 A1 | 10/2009 | Lassila |
| 2009/0304761 A1 | 12/2009 | Rabiei |
| 2010/0119564 A1 | 5/2010 | Kasuga |
| 2010/0121463 A1 | 5/2010 | Pertti |
| 2010/0168798 A1 | 7/2010 | Clineff |
| 2011/0098826 A1 | 4/2011 | Mauck |
| 2011/0166659 A1 | 7/2011 | Luginbuehl |
| 2011/0282395 A1 | 11/2011 | Beyar |
| 2012/0016373 A1* | 1/2012 | Impellizzeri ....... A61B 17/8897 606/104 |
| 2012/0040002 A1 | 2/2012 | Lehtonen |
| 2012/0040015 A1 | 2/2012 | Lehtonen |
| 2012/0040137 A1 | 2/2012 | Palasis |
| 2012/0191214 A1 | 7/2012 | Nies |
| 2012/0265206 A1 | 10/2012 | Jang |
| 2013/0144400 A1 | 6/2013 | Day |
| 2013/0204368 A1 | 8/2013 | Prevost |
| 2013/0218291 A1 | 8/2013 | Giorno |
| 2013/0296500 A1 | 11/2013 | Clay |
| 2013/0317555 A1 | 11/2013 | Schaller |
| 2015/0238655 A1 | 8/2015 | Jongpaiboonkit |
| 2015/0245901 A1 | 9/2015 | Dougherty |
| 2015/0289979 A1 | 10/2015 | Gabele |
| 2016/0011369 A1 | 1/2016 | Doyle |
| 2016/0113695 A1 | 4/2016 | Globerman |
| 2016/0135801 A1 | 5/2016 | Lombardo |
| 2016/0278789 A1 | 9/2016 | Garvey |
| 2017/0181785 A1 | 6/2017 | Beyar |
| 2017/0246356 A1 | 8/2017 | Preiss-Bloom |
| 2019/0261974 A1 | 8/2019 | Arai |
| 2021/0022725 A1 | 1/2021 | Burkhart |
| 2021/0128137 A1 | 5/2021 | Rogers |
| 2021/0161571 A1 | 6/2021 | Haziza |
| 2021/0205505 A1 | 7/2021 | Preiss-Bloom |
| 2021/0299332 A1 | 9/2021 | Dias |
| 2021/0338225 A1 | 11/2021 | Patel |
| 2022/0008615 A1 | 1/2022 | Cige |
| 2022/0079576 A1 | 3/2022 | Rogers |
| 2023/0380829 A1 | 11/2023 | Zeevi |

FOREIGN PATENT DOCUMENTS

| | | |
|---|---|---|
| CN | 1371664 A | 10/2002 |
| CN | 1565396 A | 1/2005 |
| CN | 1593356 A | 3/2005 |
| CN | 1668255 A | 9/2005 |
| CN | 1953719 A | 4/2007 |
| CN | 101106957 A | 1/2008 |
| CN | 101420991 A | 4/2009 |
| CN | 101437467 A | 5/2009 |
| CN | 101790559 B | 7/2010 |
| CN | 101942709 A | 1/2011 |
| CN | 102281907 A | 12/2011 |
| CN | 102395329 A | 3/2012 |
| CN | 102421463 A | 4/2012 |
| CN | 102421716 A | 4/2012 |
| CN | 103747813 A | 4/2014 |
| CN | 104188706 A | 12/2014 |
| CN | 106392332 A | 2/2017 |
| EP | 0373294 A2 | 6/1990 |
| EP | 1716874 A2 | 11/2006 |
| EP | 2243500 A1 | 10/2010 |
| EP | 2243749 A1 | 10/2010 |
| EP | 2292166 A1 | 3/2011 |
| EP | 17819487 | 6/2017 |
| EP | 3236866 | 11/2017 |
| EP | 3320877 A1 | 5/2018 |
| EP | 3678566 | 7/2020 |
| EP | 3689259 | 8/2020 |
| JP | 6415040 | 1/1989 |
| JP | H02121652 | 5/1990 |
| JP | 2002501418 A | 1/2002 |
| JP | 2004160157 | 6/2004 |
| JP | 2008200510 | 9/2008 |
| JP | 2009541568 | 11/2009 |
| JP | 2010526200 | 7/2010 |
| JP | 2012524569 | 10/2012 |
| WO | 9609014 A1 | 3/1996 |
| WO | 1996009014 | 3/1996 |
| WO | 9819616 | 5/1998 |
| WO | 1998019617 A1 | 5/1998 |
| WO | 9853768 A1 | 12/1998 |
| WO | 0132072 | 5/2001 |
| WO | 2005077039 A2 | 8/2005 |
| WO | 2005077039 A3 | 8/2005 |
| WO | 2008095046 A2 | 8/2008 |
| WO | 2010122019 A1 | 10/2010 |
| WO | 2010122098 A2 | 10/2010 |
| WO | 2013116624 A1 | 8/2013 |
| WO | 2016035088 A1 | 3/2016 |
| WO | 2016035089 | 3/2016 |
| WO | 2016103049 A1 | 6/2016 |
| WO | 2017155956 A1 | 9/2017 |
| WO | 2018002917 | 1/2018 |
| WO | 2019049062 | 3/2019 |
| WO | 2019123462 | 6/2019 |
| WO | 2020044327 | 3/2020 |
| WO | 2023002471 | 1/2023 |

OTHER PUBLICATIONS

Chinese Office Action (including English translation) for App. No. CN201980053932.3, dated Jan. 13, 2022, 10 pages.

European Patent Office Communication pursuant to Article 94(3) EPC issued in App. No. EP18853365, dated Feb. 1, 2023, 7 pages.

ISR from PCT/IL2022/050711 dated Oct. 19, 2022, 5 pages.

(56) References Cited

OTHER PUBLICATIONS

ISR from PCT/IL2022/051252 dated Feb. 9, 2023, 5 pages.
Office Action (Final Rejection) dated Feb. 22, 2023 for U.S. Appl. No. 17/152,165 (pp. 1-15).
Office Action (Notice of Allowance and Fees Due (PTOL-85)) dated Feb. 15, 2023 for U.S. Appl. No. 16/951,109 (pp. 1-8).
WOISA from PCT/IL2022/051252 dated Feb. 9, 2023, 8 pages.
WOSA from PCT/IL2022/050711 dated Oct. 19, 2022, 6 pages.
Indian Examination Report for App. No. IN201827049363, dated Nov. 18, 2021, 5 pages.
Indian Examination Report issued in App. No. IN202027011276, dated Apr. 27, 2022, 7 pages.
International Search Report issued in PCT/IL2019/050843, dated Nov. 6, 2019, 3 pages.
IP Office of Singapore Written Opinion for Application No. SG11201610671P, dated Aug. 14, 2019, 5 pages.
Japanese Office Action (includig English translation) issued in App. No. JP2020-511984, dated Aug. 2, 2022, 13 pages.
Japanese Office Action (including English translation) for App. No. JP2018-567587, dated Jan. 5, 2022, 5 pages.
Japanese Office Action (with English language translation) for Application No. 2017-504425, dated May 28, 2019, 7 pages.
Japanese Office Action (with English language translation) for Application No. JP2017-504425, dated Jan. 7, 2020, 6 pages.
Japanese Office Action (with English language translation) for Application No. JP2017-527796, mailing date Nov. 6, 2019, 6 pages.
Juan David Vanegas-Jaramillo, Iván David Patiño-Arcilaa, Fragmentation model for the tensile response of unidirectional composites based on the critical number of fiber breaks and the correction of the fiber-matrix interfacial strength Latin American Journal of Solids and Structures, 2019, 16(7), e217, 27 pages.
Jurij Štalc, Luke D. Cicchinelli, Stuart Miller, Carolyn M. Sofka, Martinus Richter Fiber-reinforced fixation implant for proximal interphalangeal joint arthrodesis shows advanced implant biointegration at 2-year follow-up Foot Ankle Surg. Jun. 23, 2022:S1268-7731(22)00117-5, 7 pages.
Korean Office Action (including English translation) for App. No. KR10-2019-7001863, dated Jan. 20, 2022, 13 pages.
Korean Office Action issued in App. No. KR10-2017-7018042, dated Aug. 17, 2022, 7 pages.
Kulkova J. et al. "Hydroxyapatite and bioactive glass surfaces for fiber reinforced composite implants via surface ablation by Excimer laser" (2017) Journal of the Mechanical Behavior of Biomedical Materials, vol. 75, pp. 89-96, DOI: 10.1016/j.jmbbm.2017.07.005 (published on-line Jul. 4, 2017).
Li Sijiao, "Modern Chromatographic Analysis", p. 118, National Defense Industry Press, Jun. 2014 (3 pages).
Miwa, M., Horiba, N. Effects of fiber length on tensile strength of carbon/glass fiber hybrid composites. Journal of Materials Science 29, 973-977 (1994).
Miwa, M., Ohsawa, T., and Tahara, K. (1980), Effects of fiber length on the tensile strength of epoxy/glass fiber and polyester/glass fiber composites. J. Appl. Polym. Sci., 25: 795-807 (Abstract).
Notice of Allowance dated Aug. 20, 2020 for U.S. Appl. No. 15/509,301 (pp. 1-9).
Notice of Allowance dated Aug. 28, 2020 for U.S. Appl. No. 16/081,605 (pp. 1-14).
Notice of Allowance dated Oct. 22, 2020 for U.S. Appl. No. 15/523,389 (pp. 1-6).
Office Action (Final Rejection) dated Oct. 28, 2022 for U.S. Appl. No. 16/951,109 (pp. 1-7).
Office Action (Non-Final Rejection) dated Jul. 21, 2022 for U.S. Appl. No. 16/951,109 (pp. 1-8).
Office Action (Non-Final Rejection) dated Nov. 7, 2022 for U.S. Appl. No. 17/152,165 (pp. 1-15).
Office Action (Non-Final Rejection) dated Nov. 25, 2022 for U.S. Appl. No. 16/770,091 (pp. 1-22).
Office Action (Notice of Allowance and Fees Due (PTOL-85)) dated Jan. 18, 2022 for U.S. Appl. No. 16/637,363 (pp. 1-9).
Office Action (Notice of Allowance and Fees Due (PTOL-85)) dated Feb. 8, 2022 for U.S. Appl. No. 16/311,784 (pp. 1-6).
Office Action (Notice of Allowance and Fees Due (PTOL-85)) dated Feb. 22, 2022 for U.S. Appl. No. 16/311,784 (pp. 1-3).
Office Action (Notice of Allowance and Fees Due (PTOL-85)) dated Mar. 29, 2022 for U.S. Appl. No. 16/637,363 (pp. 1-6).
Office Action dated Apr. 7, 2021 for U.S. Appl. No. 16/311,784 (pp. 1-11).
Office Action dated Aug. 5, 2019 for U.S. Appl. No. 15/509,274 (pp. 1-19).
Office Action dated Dec. 26, 2019 for U.S. Appl. No. 15/509,274, 18 pages.
Office Action dated Feb. 10, 2020, for U.S. Appl. No. 16/081,605 (pp. 1-17).
Office Action dated Jan. 13, 2020 for U.S. Appl. No. 15/523,389 (pp. 1-11).
Office Action dated Jul. 13, 2020 for U.S. Appl. No. 15/523,389 (pp. 1-12).
Office Action dated Nov. 18, 2019 for U.S. Appl. No. 16/081,605 (pp. 1-19).
Office Action dated Nov. 19, 2020 for U.S. Appl. No. 16/311,784 (pp. 1-14).
Office Action dated Nov. 7, 2019 for U.S. Appl. No. 15/523,389 (pp. 1-11).
Office Action dated Sep. 23, 2021 for U.S. Appl. No. 16/311,784 (pp. 1-11).
P. Amuthakkannan, V. Manikandan, J.T. Winowlin Jappes, M. Uthayakumar Effect of Fibre Length and Fibre Content on Mechanical Properties of Short Basalt Fibre Reinforced Polymer Matrix Composites Materials Physics and Mechanics 16 (2013) 107-117.
Polymer-Matrix Composites: Structure and Processing Deborah D.L. Chung, in Carbon Composites (Second Edition), 2017 3.3.4 Fiber Fragmentation Testing, 13 pages.
Rodricks CW, Greenfeld I, Fiedler B, Wagner HD. Fragmentation of Beaded Fibres in a Composite. Materials (Basel). Jan. 24, 2022;15(3):890, 22 pages.
Scholz et al., "The use of composite materials in modern orthopaedic medicine and prosthetic devices: A review", Composites Science and Technology, Elsevier, Amsterdam, NL, www.elsevier.com/locate/compscitech, vol. 71, No. 16 (2011) pp. 1791-1803.
Search report for parent PCT application No. PCT/IL2015/050903, mailed on Jan. 7, 2016 (13 pages).
Shia, David & Hui, Chung Yuen & Phoenix, S . . . (2000). Statistics of fragmentation in a single-fiber composite under matrix yielding and debonding with application to the strength of multi-fiber composites. Composites Science and Technology. 60. 2107-2128. 10.1016/S0266-3538(00)00115-9. (Abstract) 7 pages.
Shiqiang Deng, Lin Ye, Yiu-Wing Mai, Hong-Yuan Liu, Evaluation of fibre tensile strength and fibre/matrix adhesion using single fibre fragmentation tests, Composites Part A: Applied Science and Manufacturing, vol. 29, Issue 4, 1998, pp. 423-434 (Abstract).
Supplementary European Search Report for EP15837823 dated Mar. 28, 2018, 6 pgs.
Wang et al., "Promising Poly(E-caprolactone) composite reinforced with weft-knitted polyester for small-diameter vascular graft application", Advances in Materials Science and Engineering, 2014, vol. 2014, p. 273891, 11 pages.
Website downloaded Aug. 23, 2022 (https://www.orthobullets.com/basic-science/9062/material-properties) 11 pages.
Wegener et al., "Microstructure, cytotoxicity and corrosion of powder-metallurgical iron alloys for biodegradable bone ematerials", Materials Science & Engineering. B. Advanced Functional Solid-State Materials, 2011, vol. 176, No. 20, p. 1789-1796.
Wei Junjie, "Medical Organic Chemistry Learning Guide", p. 300, Heilongjiang Science and Technology Press, Jan. 19 (7 pages).
Arthrex Inc., "BioComposite Interference Screws—A Stronger turn in ACL/PCL Reconstruction", Scientific Research and Development, (20100000), URL: http://www.arthrex.com/knee/biocomposite-interference-screws. (6 pages).
Australian Examination Report No. 1 for App. No. AU2017287968, dated Aug. 31, 2021, 3 pages.
Australian Examination Report No. 1 for App. No. AU2017287968, dated Feb. 12, 2021, 4 pages.

(56) References Cited

OTHER PUBLICATIONS

Australian Examination Report No. 1 for Application No. 2015310510, dated Aug. 10, 2019, 6 pages.
Australian Examination Report No. 1 for Application No. AU2015370600, dated Oct. 2, 2019, 3 pages.
Australian Examination Report No. 2 for Application No. AU2015310510, dated Dec. 1, 2019, 3 pages.
Australian Examination Report No. 2 for Application No. AU2015370600, dated Jan. 29, 2020, 2 pages.
Brazilian Search Report (with English language translation) for App No. BR112017001049-6, dated Apr. 8, 2020, 8 bages.
Brazilian Technical Report (with English language translation) for App No. BR112017012508-0, dated Apr. 8, 2020, 7 pages.
C. Capelaa, S. E. Oliveiraa, J. Pestanaa, J.A.M. Ferreira, "Effect of fiber length on the mechanical properties of high dosage carbon reinforced", Procedia Structural Integrity 5 (2017) 539-546.
Canadian Office Action for App. No. CA2,955,392, dated Sep. 27, 2021, 15 pages.
Canadian Office Action issued in App. No. CA2,955,392, dated May 31, 2022, 4 pages.
Chinese Office Action (including English translation) for App. No. CN201780025291.1, dated Aug. 10, 2021, 12 pages.
Chinese Office Action (including English translation) for App. No. CN201780025291.1, dated Jan. 28, 2021, 12 bages.
Chinese Office Action (including English translation) issued in App. No. CN201880057783.3, dated Aug. 2, 2022, 16 bages.
Chinese Office Action (with English language translation) for App No. CN201580070362.0, datetd May 20, 2020, 9 pages.
Chinese Office Action (with English language translation) for Application No. 201580036606.3, dated Mar. 12, 2019, 13 pages.
Chinese Office Action (with English language translation) for Application No. CN201580036606.3, dated Oct. 25, 2019, 9 pages.
Chinese Office Action (with English language translation) for Application No. CN201580037255.8, dated Aug. 26, 2019, 16 pages.
Chinese Office Action (with English language translation) for Application No. CN201580070362.0, dated Aug. 29, 2019, 10 pages.
Chinese Office Action (with English translation) for App. No. CN201780053086.6, dated May 7, 2022, 21 pages.
Chinese Office Action (with English translation) for App. No. CN201780053086.6, dated Oct. 19, 2021, 15 pages.
Chinese Office Action dated Jul. 13, 2018 for corresponding CN Patent Application No. 201580037255.8, 9 pages.
Chinese Office Action for App. No. CN201780053086.6, dated Feb. 18, 2021, 23 pages.
Chinese Office Action for App. No. CN201880057783.3, dated Dec. 2, 2021, 15 pages.
Chinese Office Action for Appl. No. 201580037255.8, dated Mar. 26, 2019, 7 pages.
Chinese Third Office Action (with English translation) for App. No. CN201780053086.6, dated Feb. 16, 2022, 13 pages.
Composites Encyclopedia, WO Dingzhu et al., pp. 519-520, Beijing: Chemical Industry Press, Jan. 2001, (pp. 7-12).
Corrected Notice of Allowability dated Dec. 23, 2020 for U.S. Appl. No. 15/523,389 (pp. 1-3).
Corrected Notice of Allowability dated Oct. 19, 2020 for U.S. Appl. No. 16/081,605 (pp. 1-9).
Corrected Notice of Allowability dated Oct. 7, 2020 for U.S. Appl. No. 15/509,301 (pp. 1-6).
English translation of Chinese Office Action issued in App. No. CN201780025291.1, dated Apr. 9, 2022, 6 pages.
English translation of Chinese Office Action issued in App. No. CN201880057783.3, dated Dec. 2, 2021, 11 pages.
English translation of Japanese Office Action for App. No. JP2018-567587, dated Mar. 23, 2021, 4 pages.
English translation of Japanese Office Action issued in App. No. JP2018-567587, dated Jul. 5, 2022, 4 pages.
English translation of Japanese Office Action issued in App. No. JP2020-534895, dated Oct. 4, 2022, 3 pages.
European Patent Office Communication pursuant to Article 94(3) EPC for App. No. EP17763876.4, dated Aug. 19, 2020, 9 pages.
European Patent Office Communication pursuant to Article 94(3) EPC for App. No. EP17763876.4, dated Jan. 4, 2022, 8 pages.
European Patent Office Communication pursuant to Article 94(3) EPC for App. No. EP17819487.4, dated Jun. 21, 2021, 5 pages.
European Search Report and Written Opinion dated Jun. 12, 2018 for EP Application No. 158720441, 5 pages.
European Search Report dated Oct. 16, 2019 for EP Application No. 17763876.4, 11 pages.
European Search Report for EP15838477.6 dated Mar. 5, 2018, 5 pages.
Extended European Search Report for App. No. EP18853365.7, dated May 4, 2021, 7 pages.
Extended European Search Report for App. No. EP18890927.9, dated Jul. 27, 2021, 7 pages.
Extended European Search Report for Application No. EP17819487.4, dated Feb. 4, 2020, 7 pages.
Extended European Search Report for Application No. EP19200585.8, dated Feb. 28, 2020, 8 pages.
Extended European Search Report issued in App. No. EP22185127, dated Dec. 15, 2022, 9 pages.
Feih, S., Wonsyld, K., Minzari, D., Westermann, P., & Lilholt, H. (2004). Testing Procedure for the Single Fiber Fragmentation Test. Risø National Laboratory. Denmark. Forskningscenter Risoe. Risoe-R No. 1483(EN) 31 pages.
Ferri JM et al., "The effect of beta-tricalcium phosphate on mechanical and thermal performances of poly(lactic acid)", J Composite Materials 2016; 0(0): 1-10.
Hyon et al., "Effects of Residual Monomer on the Degradation of DL-Lactide Polymer" Polymer International 46 (1998) 196-202.

* cited by examiner

CANNULATED IMPLANT DELIVERY DEVICE WITH ADJUSTABLE INSERTION DEPTH

FIELD OF THE INVENTION

The present invention is of a device, system and method for implant delivery, and in particular, to such a device, system and method for delivery of an implant having an adjustable insertional depth.

BACKGROUND OF THE INVENTION

Medical implants can be delivered or inserted using a variety of insertion devices. For example, threaded implants such as screws can be mounted on a driver and inserted into a tissue, such as, a bone tunnel by rotation. Straight implants, such as pins, can be tamped into a bone tunnel through a sleeve using a mallet to tamp the implant directly or to tamp a rod that pushes the implant into place. Sometimes, the medical implant is cannulated and the implant is inserted over a Kirschner wire (k-wire) such that the wire leads the implant in a specific trajectory into the bone tunnel. In such cases that the medical implant is cannulated, the insertion device (driver or tamp) will also generally be cannulated so as to allow the k-wire to pass through the body of the insertion device as the device is inserting the implant into the bone or bone tunnel.

The depth of insertion of a medical implant may be determined by implant design or by how far the surgeon chooses to insert the implant. For a headed screw, an example of an implants with an insertion depth determined by implant design, the surgeon can only insert the screw until the head reaches the bone surface. The screw has then reached its terminal depth in the bone and will not proceed further. Similarly, a nail with a head could only be tamped until the head becomes lodged in the bone surface. With a headless screw or with a pin, the surgeon can choose to continue inserting the implant even as the implant goes into the bone. The implant will progress deeper and deeper into the bone as the surgeon rotates the driver with a screw or tamps the implant with a pin until the surgeon chooses to stop inserting. In some cases, a fixed stopper may be provided on the inserter device to only allow insertion of the implant to a present, fixed depth.

BRIEF SUMMARY OF THE INVENTION

The background art does not teach or suggest a device, system or method for delivery of an implant to an adjustable depth of insertion. The background art also does not teach or suggest such a device, system or method for measurement of an appropriate length for an implant. The background art also does not teach or suggest a single insertion device that would allow for the insertion of a medical implant to an insertion depth that is adjustable to the desired depth of the surgeon, within a fixed preset range.

The present invention, in at least some embodiments, overcomes these drawbacks of the background art by providing a device, system and method for delivery of an implant to an adjustable depth of insertion. The device comprises a cannula for receiving a guide or depth finding placeholder, including but not limited to, a guide wire, such as a K-wire for example. The cannula preferably comprises an opening of sufficient diameter to permit insertion of the depth finding placeholder. The cannula comprises depth indicators, for example by being optionally marked with depth indicator markings. The device preferably comprises a transparent window, or optionally may comprise, additionally or alternatively, an open aperture and/or a viewing screen, to enable the depth indicators to be viewed.

The depth finding placeholder, such as the guide wire, may be placed in an opening in a tissue. The tissue may comprise bone, tendon, cartilage and the like. Once the wire has been placed within the opening to the correct depth, the cannula of the device preferably slides over the wire. The markings on the cannula indicate the depth to which the depth finding placeholder or guide has been inserted into the tissue, and hence the preferred length of the implant. The length of the implant may then be measured using the device of the present invention and adjusted appropriately, according to the measured depth, for example and without limitation, by cutting the implant using cutting tools known in the art such as a vibrating saw, reciprocating saw, bone cutters, scalpel, etc. The implant may then be inserted into the tissue by tamping or screwing.

The implant delivery or insertion device of the present invention also optionally and preferably incorporates an adjustable depth of insertion element that prevents the insertion device for inserting the implant past a depth that is determined by the user (surgeon) adjusting the element to fix the depth of insertion prior to insertion. This insertion element allows adjustment within a preset fixed range. Preferably, the range allows for the user to adjust depth of insertion from flush with the tissue (i.e. implant can only be inserted until it is completely within the tissue) to sunk below the surface of the tissue.

Preferably the implant itself is cannulated, for example for guiding the implant along the depth finding placeholder, such as the guide wire.

Without wishing to be limited to a closed list, these embodiments of the present invention overcome the limitations of the background art that allowed for either a single fixed depth of insertion (fixed depth implant or fixed depth insertion device) or no guidance to set depth of insertion (freehand implant insertion); as well as allowing the user (surgeon) to achieve precisely the depth level of insertion that is optimal for that specific surgery, whether it be insertion that is flush with the bone or insertion that sinks the implant several mm below the surface of the bone; and, by optionally incorporating a depth measuring gauge, is also able to both allow the measuring of the desired implant length prior to insertion and also optionally measure the depth of insertion during insertion.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings.

DESCRIPTION OF THE INVENTION

Figure 1:
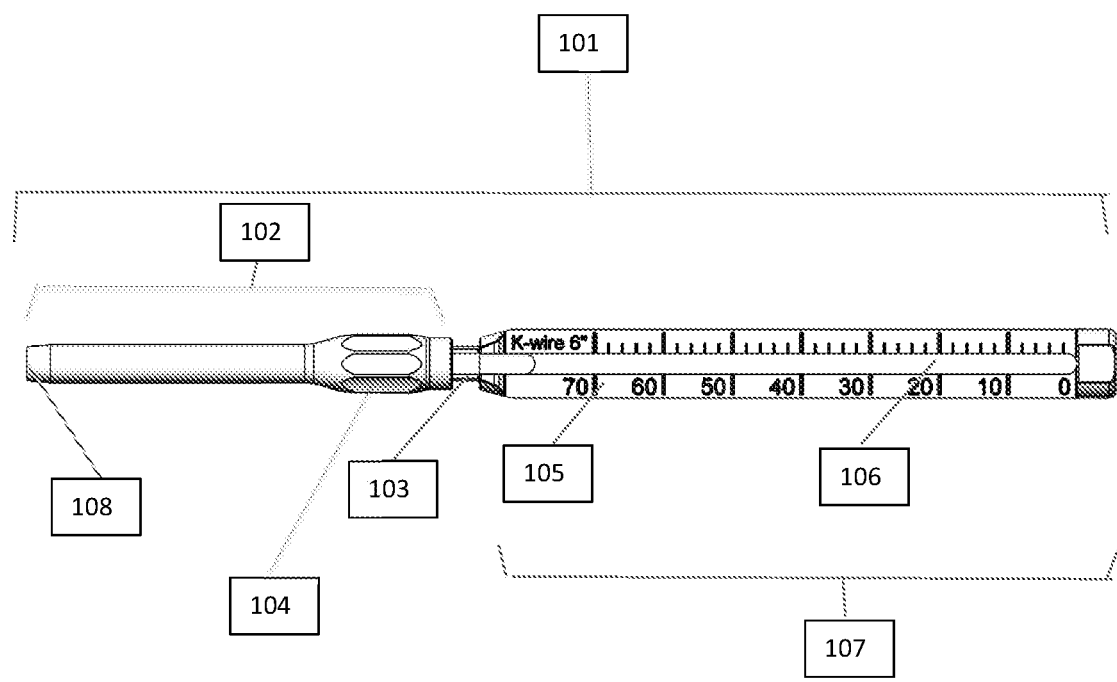
FIG. 1 shows a non-limiting example of a cannulated implant insertion device for determining an appropriate length of an implant and having an adjustable portion to set insertion depth of implant.

The present invention and at least some embodiments relates to an implant delivery device with a measuring scale.
Definitions As used herein the terms "implant cavity", "bone tunnel" and "drill hole" can be used interchangeably to mean a cavity in the tissue which is created, such as, with a drill at a desired shape and size for the implant insertion. The implant cavity can be, for example, drilled into bone or soft tissue.

As used herein "cannulated" means having a hollow center, for example, in the form of a tube.

Biocomposite medical implants useful for use with the present invention have been previously described in WO 2016/035088, WO 2016/035089, WO 2016/103049, WO 2017/155956, WO 2018/002917, WO2019/049062, WO 2019/123462 and WO2020/0044327 the entire contents of each of which are incorporated herein by reference.
Devices of the Present Invention:

In one embodiment the present invention is an implant delivery device for introducing and positioning an implant within a subject. In one embodiment, the implant of the present invention is in the form of a handheld assembly which includes a device body in the form of an elongated shaft having a distal end and a proximal end. In one embodiment, there is a cannulated cavity in the elongated shaft at the proximal end and a measuring element at the distal end.

In one embodiment, the measuring element comprises a solid portion and a hollow space formed by a recess in the solid portion. In one embodiment, the recess is sized to accommodate a guide, such as, a guide wire or Kirschner wire (k-wire) (also known herein as a depth finding placeholder) and/or an implant. In one embodiment, the solid portion further comprises a scale for measuring the length of a guide and/or an implant. In one embodiment, a guide can pass through the cannulated cavity in the elongated shaft from the proximal end of the device through to the recess in the measuring element. In one embodiment the solid portion of the measuring element is in the shape of a cylindania with a flat surface comprising a scale and a second flat surface opposite the scale to prevent the device rolling if placed on a flat surface. In one embodiment, the device is passed over a guide wire which has been inserted in the tissue of a subject, the device is passed down the length of the guide wire into the body of the subject until the device is flush with the tissue surface. The length of guide wire exposed in the recess of the measuring element is then measured using the measuring scale and the length of implant needed is determined from the length of wire exposed.

In one embodiment the proximal end of the device is the end inserted into the subject nearest the tissue receiving the implant. In one embodiment the distal end is the end furthest from the tissue receiving the implant and closest to the user (surgeon).

In one embodiment, the device comprises an adjustable depth of insertion element at the proximal end. In one embodiment, the adjustable depth of insertion element is in the shape of a tube which can slide up and down the elongated shaft between the proximal end of the device and the measuring element. In one embodiment, the movement of the adjustable depth of insertion element up and down the elongated shaft is controlled using a rotatable dial knob on the adjustable depth insertion element which rotates the adjustable depth of insertion element relative to the device body. In one embodiment, the dial knob moves the depth of insertion element by rotating on internal threads to move the depth of insertion element proximally and distally along the length of the elongated shaft to control the insertion depth of the implant.

In one embodiment, the device further comprises an abutment surface at the proximal end of the adjustable depth of insertion element. In one embodiment, the diameter of the abutment surface is larger than the diameter of the implant cavity. In one embodiment, the abutment surface abuts the tissue, such as, the bone of the subject and prevents the device from entering the implant cavity in the tissue. In one embodiment, the abutment surface abuts the tissue when the adjustable depth of insertion element is fully extended towards the proximal end of the device and none of the elongated shaft is exposed at the proximal end of the device beyond the abutment surface. In one embodiment, for implant insertion flush with the bone surface the abutment surface is larger than the implant cavity. In one embodiment, the abutment surface is 1 mm to 10 mm, 2 mm to 8 mm, 3 mm to 6 mm in diameter.

In one embodiment, the elongated shaft at the proximal end of the device body has a diameter smaller than or equal to the diameter of the implant cavity. In one embodiment of the present invention, the device can be used with the adjustable depth of insertion element fully or partially retracted back to the measuring element, exposing the up to the maximum amount of elongated shaft at the proximal end of the device beyond the abutment surface of the adjustable depth of insertion element. In one embodiment of the present invention, the device can be used with adjustable depth of insertion element fully or partially retracted back to the measuring element in order to position the implant below the surface of the tissue, such as the bone of a subject. In one embodiment, for implant insertion below the bone surface the diameter of the proximal end of the elongated shaft is equal to or smaller than the diameter of the implant cavity. In one embodiment, the proximal end of the elongated shaft is 0.5 mm to 5 mm, 1 mm to 4 mm, 2 mm to 3 mm in diameter. In one embodiment, the proximal end of the elongated shaft extending beyond the abutment surface of the adjustable depth of insertion element is 1 mm to 6 mm, 2 mm to 5 mm, 3 mm 4 mm in length.

In one embodiment, the device further comprises a cap at the distal end. In one embodiment, the implant is inserted into the desired location by a manually applicable directional pressure on the cap at the distal end of the device, such as, banging the cap with a mallet.

In one embodiment, the cannulated cavity in the proximal end of the device is accessible through an opening formed at the proximal end and extending along the longitudinal axis of the implant delivery device through to the recess of the measuring element.

In one embodiment, the device is used with a guide (depth finding placeholder) that guides positioning of the implant relative to the desired delivery site, such as the bone of the subject. In one embodiment, the cannulated cavity of the device is sized to receive the guide. In one embodiment, the guide is a guide wire, such as a Kirschner wire (k-wire) or pin. In one embodiment, the implant is inserted into the desired location by a manually applicable directional pressure on the cap at the distal end of the device in the direction of the guide.

In one embodiment, the implant delivery device comprises a carbon fiber composite or a metal such as stainless steel, titanium, or an alloy or composite thereof.

In one embodiment, the implant delivery device is between about 100 mm to 300 mm, 120 mm to 200 mm, 130 mm to 180 mm in length.

In one embodiment, the implant delivery device is between about 5 mm to 30 mm, 6 mm to 20 mm, 8 mm to 12 mm in diameter.

FIG. 1 shows a non-limiting example of a cannulated device for determining an appropriate insertional depth of an implant having an adjustable portion to set insertion depth of the implant. As shown, a device body 101 comprises a dial knob 104 on an adjustable length of insertion element 102 which can be rotated to move the adjustable length of insertion element distally or proximally along the elongated shaft 103. An abutment surface 108 at the tip of the adjustable length of insertion element is used to abut a tissue to prevent the device from progressing into the implant cavity. A measuring element 107 comprises a measuring scale 105 which accommodates measurement of the required length of the implant; and a recess 106 for holding a guide wire and/or an implant to measure the length of wire insertion in the tissue (from which the user can determine the length of implant that is needed).

Figure 2:
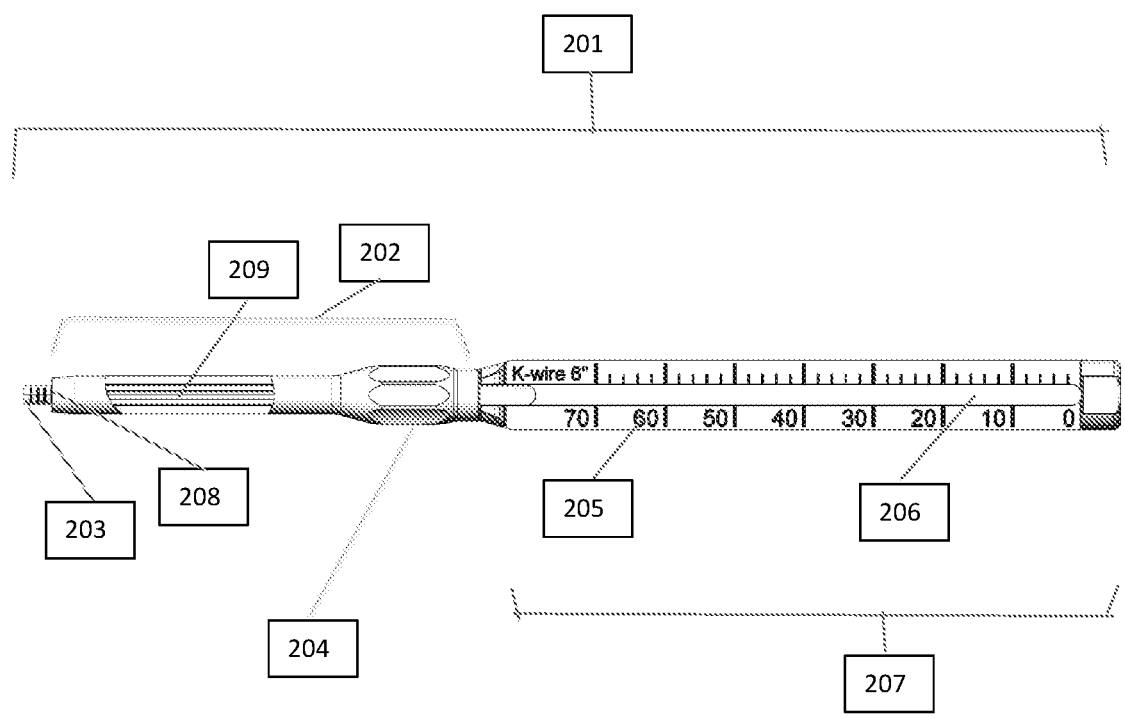
FIG. 2 shows a cut-away view of the cannulated implant insertion device for determining an appropriate length of an implant and having an adjustable portion to set insertion depth of implant.

FIG. 2 shows a cut-away view of the cannulated device for determining an appropriate insertional depth of an implant having an adjustable portion to set insertion depth of implant. As shown, a device body 201 comprises a cannulated cavity 209 which allows the device to be passed over a guide, such as a wire. Device body 201 also comprises an dial knob 204 on an adjustable length of insertion element 202 that allows the user to set the desired insertional depth of the implant with respect to the tissue surface. An elongated shaft segment 203 that is smaller or equal in diameter to the implant cavity into which the implant is being inserted allows the implant to be embedded below the bone or other tissue surface when it is exposed at the proximal end of the device beyond the abutment surface 208 of the adjustable length of insertion element 202. In operation, turning dial knob 204 causes the adjustable length of insertion element 202 to rotate proximally or distally on internal threads such that the when the adjustable length of insertion element is fully extended to the proximal end of the device, the elongated shaft is not exposed at the proximal end of the device (as in FIG. 1); or when the adjustable length of insertion element is partially or fully retracted towards the measuring element 207 of the device the elongated shaft is partially or fully exposed, respectively, at the proximal end of the device (as in FIG. 2). Such rotation determines the extent to which elongated shaft 203 becomes exposed at either the proximal end or the measuring element end or the device. A greater length of exposure of the elongated shaft 203 at the proximal end of the device beyond the abutment surface 208 of the adjustable length of insertion element 202, enables the implant to be embedded deeper within the tissue. If the elongated shaft 203 is not exposed at the proximal end of the device beyond the abutment surface 208 of the adjustable length of insertion element 202, then the implant is placed in a flush position at the tissue surface as the maximal depth to which the implant is placed within the tissue surface. The depth of implant insertion below the tissue surface is determined by adjusting the length of the elongated shaft segment that is exposed at the proximal end of the device beyond the abutment surface 208 of the adjustable length of insertion element 202 by rotating the dial knob 204 on the adjustable length of insertion element 202. Such a tissue may be bone, for example, such that the tissue surface would be the surface of the bone. A measuring element 207 comprises a measuring scale 205 which accommodates measurement of the required length of the implant; and a recess 206 for holding a guide wire and/or an implant to measure the length of wire insertion in the tissue (from which the user can determine the length of implant that is needed).

Figure 3:
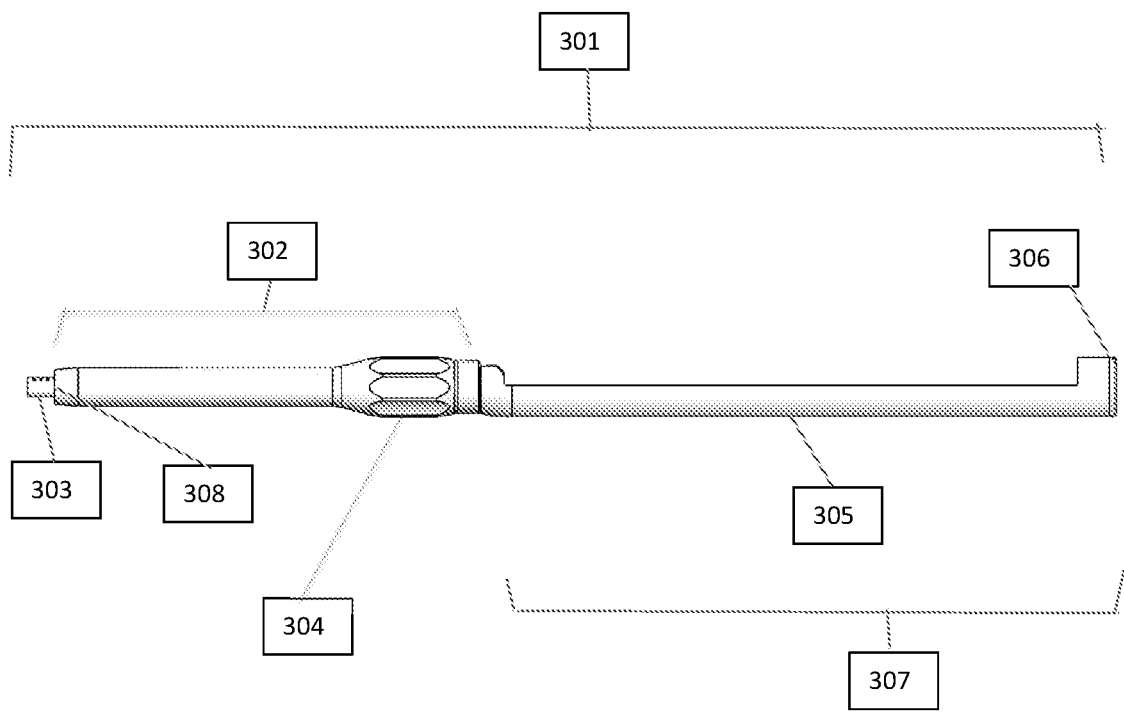
FIG. 3 shows a side view of a non-limiting example of the cannulated implant insertion device.

FIG. 3 shows a further non-limiting example of the devices of the present invention where 301 is a side view the device body, 302 is an adjustable length of insertion element comprising a dial knob 304 and an abutment surface 308, 307 is a measuring element comprising a flat surface 305 to prevent the device rolling if placed on a flat surface, and 303 is the elongated shaft which is exposed at the proximal end of the device, and 306 is the cap which can be hit with a mallet by the user to embed the implant in a bone.

Methods of Use

In one embodiment the present invention relates to device for use in a surgical procedure for delivering an implant into the bone of a subject.

In one embodiment of the present invention, the device body is removably positionable at least partially subcutaneously within the subject.

In one embodiment of the present invention, the device body releasably secures the implant during positioning of the implant. In one embodiment of the present invention, the delivery device retains the implant during delivery and detaches the implant at a target location.

In one embodiment, the implant is inserted into the subject as follows:

Step 1: place guide wire to desired depth in the desired location in the subject using a drill or manual insertion technique know in the art.

Step 2: place implant device over guide wire and measure length of implant desired.

Step 3: place the implant in the recess of the measuring device to measure and mark the implant at the desired length or trim to the desired length using a cutting device known in the art, such as a sagittal saw.

Step 4: use cannulated drill over guide wire to create implant cavity at approximate length of implant length.

Step 5: place implant over guide wire followed by implant insertion device.

Step 6: use a mallet on cap of implant device to tamp implant into implant cavity until device abutment surface reaches tissue surface.

Step 7: remove implant device and guide wire.

Step 7: cut implant flush to bone surface with a sagittal saw or other device known if the art if implant was not cut in step 3.

In one embodiment, the implant is inserted into the subject as follows:

Step 1: place guide wire to desired depth in the desired location in the subject using a drill or manual insertion technique know in the art.

Step 2: place implant device over guide wire and measure length of implant desired.

Step 3: place the implant in the recess of the measuring device to measure and mark the implant at the desired length or trim to the desired length using a cutting device known in the art, such as a sagittal saw.

Step 4: use cannulated drill over guide wire to create implant cavity at approximate length of implant length.

Step 5: rotate dial knob shaft segment to expose inserting shaft segment to desired length.

Step 6: place implant over guide wire followed by implant insertion device.

Step 7: use a mallet on cap of implant device to tamp implant into implant cavity just below bone surface, as inserting shaft segment pushes implant deeper into cavity, until insertion device abutment surface reach tissue surface.

Step 8: remove implant device and guide wire.

Statements of the Invention

1. In one embodiment the invention is a device for inserting an implant at an appropriate tissue depth according to a depth finding placeholder, wherein the implant is suitable for insertion to a subject, the device comprising an elongated shaft comprising a cannula for receiving the depth finding placeholder and an adjustable depth of insertion element, wherein the position of the adjustable depth of insertion element on the elongated shaft is adjusted to determine the appropriate implant insertion depth relative to a tissue surface.
2. The device of statement 1, wherein the adjustable depth of insertion element comprises a dial knob, wherein rotation of said dial knob exposes or covers the elongated shaft at a proximal end of the device; wherein an extent of exposure of said elongated shaft determines the implant insertion depth relative to a tissue surface.
3. The device of statement 2, wherein complete coverage of said elongated shaft at the proximal end of the device determines the appropriate implant insertion depth such that the implant is inserted flush with a surface of the tissue.
4. The device of any of the above statements, wherein a diameter of the depth of insertion element is sufficiently large to prevent insertion of the depth of insertion element into said tissue.
5. The device of any of the above statements, wherein a diameter of said elongated shaft does not exceed a diameter of the implant.
6. The device of any of the above statements, further comprising a scale to measure the length of the depth finding placeholder to determine the appropriate length of the implant.
7. The device of any of the above statements, further comprising a recess to measure the implant.
8. The device of any of the above statements, further comprising a flat surface to prevent the device from rolling.
9. The device of any of the above statements, wherein the implant is cannulated.
10. The device of statement 9, wherein the implant is a cannulated nail, pin, wire or screw.
11. The device of any of the above statements, wherein the device is 100 mm to 300 mm, 120 mm to 200 mm, or 130 mm to 180 mm in length.
12. The device of any of the above statements, wherein the device is 2 mm to 30 mm, 6 mm to 20 mm, 8 mm to 12 mm in diameter.
13. The device of any of the above statements, wherein the device comprises carbon fiber composite or a metal.
14. The device of statement 13, wherein the metal is stainless steel, titanium, or an alloy or composite thereof.
15. A system for determining an appropriate length of an implant, wherein the implant is suitable for insertion to a subject, the system comprising a depth finding placeholder and the device of claim 1; wherein the depth finding placeholder is inserted into the subject to a determine an appropriate depth for inserting the implant; wherein said cannula of said device receives the depth finding placeholder, and determines the appropriate length of the implant according to a measured length of the depth finding placeholder; and wherein said dial knob is rotated to determine exposure of said elongated shaft at a proximal end of the device, for inserting the implant at said appropriate depth.
16. The system of statement 15, wherein the depth finding placeholder comprises a wire.
17. The system of statement 16, wherein said wire comprises a K-wire.
18. An implant insertion device comprising an implant body with a proximal end and distal end, wherein the proximal end comprises an elongated shaft comprising a cannula and an adjustable depth of insertion element surrounding the elongated shaft, and wherein the distal end comprises a measuring portion comprising a recess and a measuring scale.
19. The device of statement 18, wherein the position of the adjustable depth of insertion element on the elongated shaft is adjusted to determine an implant insertion depth in a tissue.
20. The device of statement 19, wherein the adjustable depth of insertion element comprises a dial knob, wherein rotation of said dial knob moves the adjustable length of insertion element proximally or distally along the elongated shaft exposing or covering a portion of the elongated shaft at the proximal end of the device.
21. The device of any of the above statements, wherein the device is 100 mm to 300 mm, 120 mm to 200 mm, or 130 mm to 180 mm in length.
22. The device of any of the above statements, wherein the device is 2 mm to 30 mm, 6 mm to 20 mm, 8 mm to 12 mm in diameter.
23. The device of any of the above statements, wherein the adjustable depth of insertion element comprises an abutment surface.
24. The device of statement 22, wherein the abutment surface is 1 mm to 10 mm, 2 mm to 8 mm or 3 mm to 6 mm in diameter.
25. The device of any of the above statements, wherein the proximal end of the elongated shaft is 0.5 mm to 5 mm, 1 mm to 4 mm, 2 mm to 3 mm in diameter.
26. The device of any of the above statements, wherein the proximal end of the elongated shaft exposed at the proximal end of the device beyond the abutment surface of the adjustable depth of insertion element is 1 mm to 6 mm, 2 mm to 5 mm, or 3 mm 4 mm in length.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A device for inserting an implant at an appropriate tissue depth according to a depth finding placeholder, wherein the implant is suitable for insertion to a subject, the device comprising an elongated shaft comprising a cannula for receiving the depth finding placeholder and an adjustable depth of insertion element, wherein the adjustable depth of insertion element comprises a dial knob, wherein rotation of said dial knob exposes or covers the elongated shaft at a proximal end of the device; wherein an extent of exposure of said elongated shaft determines the implant insertion depth relative to a tissue surface; and wherein the position of the adjustable depth of insertion element on the elongated shaft is adjusted to determine the appropriate implant insertion depth relative to a tissue surface.

2. The device of claim 1, wherein complete coverage of said elongated shaft at the proximal end of the device determines the appropriate implant insertion depth such that the implant is inserted flush with a surface of the tissue.

3. The device of claim 1, wherein a diameter of the depth of insertion element is large enough to prevent insertion of the depth of insertion element into said tissue.

4. The device of claim 1, wherein a diameter of said elongated shaft does not exceed a diameter of the implant.

5. The device of claim 1, further comprising a scale to measure the length of the depth finding placeholder to determine the appropriate length of the implant; a recess to measure the implant; and a flat surface to prevent the device from rolling.

6. The device of claim 1, wherein the implant is cannulated.

7. The device of claim 6, wherein the implant is a cannulated nail, pin, wire or screw.

8. The device of claim 1, wherein the device is 100 mm to 300 mm, 120 mm to 200 mm, or 130 mm to 180 mm in length.

9. The device of claim 1, wherein the device is 2 mm to 30 mm, 6 mm to 20 mm, or 8 mm to 12 mm in diameter at the distal end of the elongated shaft.

10. The device of claim 1, wherein the device comprises carbon fiber composite or a metal.

11. The device of claim 10, wherein the metal is stainless steel, titanium, or an alloy or composite thereof.

12. A system for determining an appropriate length of an implant, wherein the implant is suitable for insertion to a subject, the system comprising a depth finding placeholder and the device of claim 1; wherein the depth finding placeholder is inserted into the subject to a determine an appropriate depth for inserting the implant; wherein said cannula of said device receives the depth finding placeholder, and determines the appropriate length of the implant according to a measured length of the depth finding placeholder; and wherein said dial knob is rotated to determine exposure of said elongated shaft at a proximal end of the device, for inserting the implant at said appropriate depth.

13. The system of claim 12, wherein the depth finding placeholder comprises a wire.

14. The system of claim 13, wherein said wire comprises a K-wire.

15. An implant insertion device comprising an implant body with a proximal end and distal end, wherein the proximal end comprises an elongated shaft comprising a cannula and an adjustable depth of insertion element surrounding the elongated shaft, wherein the adjustable depth of insertion element comprises a dial knob, wherein rotation of said dial knob moves the adjustable length of insertion element proximally or distally along the elongated shaft exposing or covering a portion of the elongated shaft at the proximal end of the device; and wherein the distal end comprises a measuring portion comprising a recess and a measuring scale.

16. The device of claim 15, wherein the position of the adjustable depth of insertion element on the elongated shaft is adjusted to determine an implant insertion depth in a tissue.

17. The device of claim 15, wherein the device is 100 mm to 300 mm, 120 mm to 200 mm, or 130 mm to 180 mm in length and wherein the device is 2 mm to 30 mm, 6 mm to 20 mm, or 8 mm to 12 mm in diameter at the distal end of the elongated shaft.

18. The device of claim 15, wherein the adjustable depth of insertion element comprises an abutment surface; and wherein the abutment surface is 1 mm to 10 mm, 2 mm to 8 mm or 3 mm to 6 mm in diameter.

19. The device of claim 15, wherein the proximal end of the elongated shaft is 0.5 mm to 5 mm, 1 mm to 4 mm, or 2 mm to 3 mm in diameter.

20. The device of claim 15, wherein the proximal end of the elongated shaft exposed at the proximal end of the device beyond the abutment surface of the adjustable depth of insertion element is 1 mm to 6 mm, 2 mm to 5 mm, or 3 mm 4 mm in length.

* * * * *